United States Patent [19]

Ochsner

[11] 4,116,970
[45] Sep. 26, 1978

[54] N-2-HYDROXYETHYL-OXAZOLIDINE COMPOUND

[75] Inventor: Paul Albert Ochsner, Geneva, Switzerland

[73] Assignee: Givaudan Corporation, Clifton, N.J.

[21] Appl. No.: 811,915

[22] Filed: Jun. 30, 1977

[30] Foreign Application Priority Data

Jul. 12, 1976 [AT] Austria .................................. 5109/76

[51] Int. Cl.² .......................................... C07D 263/04
[52] U.S. Cl. ............................. 260/307 FA; 260/598
[58] Field of Search .................................. 260/307 FA

[56] References Cited

U.S. PATENT DOCUMENTS 3,935,205  1/1976  Ochsner ........................... 260/246 B

OTHER PUBLICATIONS

Mousseron-Canet et al. Bull. Soc. Chim. France (1956), pp. 391–401.
Ohloff-Annalen der Chemie 606 (1957), pp. 100–123.
Arctander-"Perfume and Flavor Chemicals I" - Published by Author, (1969), Nos. 1754 and 2162.

Primary Examiner—Raymond V. Rush
Attorney, Agent, or Firm—Thomas Cifelli, Jr.; Robert F. Tavares

[57] ABSTRACT

Compounds of the formula:

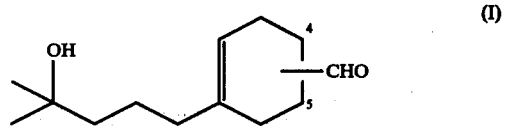

are made by hydrating a compound of the formula

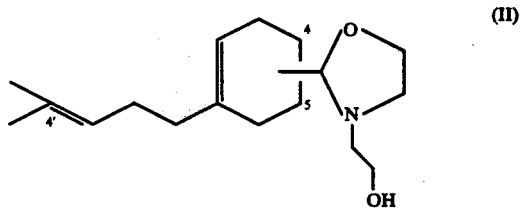

and splitting off the oxazolidinyl protecting group.
Compounds of formula II are prepared by reacting a compound of the formula:

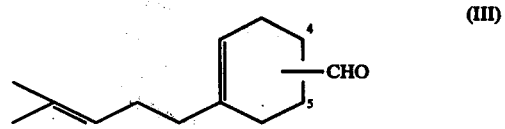

with diethanolamine.

1 Claim, No Drawings

N-2-HYDROXYETHYL-OXAZOLIDINE COMPOUND

FIELD OF THE INVENTION

This invention relates to olfactory materials and imtermediates therefor.

SUMMARY OF THE INVENTION

See the foregoing "Abstract of the Disclosure."

DESCRIPTION OF THE PREFERRED EMBODIMENTS

The process provided by the present invention comprises hydrating a compound of the formula:

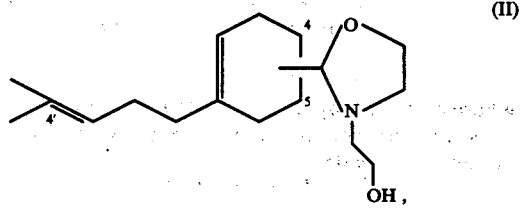

where the N-2-hydroxyethyl-oxazolidinyl group is in the 4- or 5-position, or mixtures of the 4- and 5-position isomers of formula II by means of 50-65% sulphuric acid to the corresponding 4'-hydroxy compound and subsequently splitting off the N-2-hydroxyethyl-oxazolidinyl protecting group.

The surprising nature of the present process becomes clear when one considers the lack of success which attends attempts to carry out the hydration step with other agents customarily used for hydration purposes. When such agents are used, either no reaction, or cyclisation, polymerisation or even resinification occurs. This is, very surprisingly, also the case when sulphuric acid below 50% or above 65% is used. In particular, the following agents have been found to be unsuitable for purposes of this invention:

| | |
|---|---|
| $H_2SO_4$ | 20%   40%   80%   90% |
| HCl | dilute (2-N); concentrated |
| $H_3PO_4$ | 60% 85% |
| HCOOH | dilute (2-N); concentrated |
| $CH_3COOH$ | dilue; concentrated |
| $CH_3COOH$ (concentrated)/$H_2SO_4$ | (small amount) |
| Oxalic acid | 50% |
| p-Toluenesulphonic acid/water | (50:50) |
| Methanesulphonic acid/water | (50:50) |
| $BF_3$ | |

The hydration can be carried out at a temperature in the range of from approximately −20° C. to +30° C., preferably at a temperature of from approximately 0° C. to approximately +20° C.

The splitting off of the N-2-hydroxyethyl-oxazolidinyl protecting group can be carried out in accordance with methods known per se, conveniently by adjusting the pH value of the mixture obtained after carrying out the hydration to a range of approximately 5 to 7, especially 6, for which purpose an aqueous alkali metal hydroxide solution (e.g. sodium hydroxide solution) is suitable. The splitting off of the protecting group is conveniently carried out at a slightly elevated temperature (e.g. between approximately 20° C. and 40° C.). The presence of a water-immiscible organic solvent such as methylene chloride, ethylene chloride, benzene, toluene etc is convenient.

The compound of formula II (or the corresponding 4- and 5-position isomer mixtures) can be prepared by reacting a compound of the formula

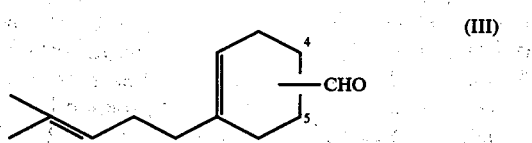

wherein the formyl group is in the 4- or 5-position, or mixtures of the 4- and 5-position isomers of formula III with diethanolamine.

In the aforementioned reaction, the diethanolamine is conveniently used in an equimolecular amount, but preferably in 1% to 10% excess.

The reaction is preferably carried out at a temperature in a range of from approximately 30° C. to 50° C.

The technical advantage of the process provided by the present invention is that the oxazolidine of formula II can be directly subjected to the hydration without purification.

The compounds of formula I and mixtures of the 4- and 5-position isomers of formula I are known and are valuable odorants which find varied applications in the odorant industry; see, for example, S. Arctander, Perfume and Flavor Chemicals I, 1754 (Montclair, N.J. 1969).

The compounds of formula II and their isomer mixtures are novel and also form part of the present invention. They are valuable starting materials for the process provided by this invention.

The following Example illustrates the present invention:

EXAMPLE 192 g (1 mol) of 4-(4-methyl-3-pentenyl)-$\Delta^3$-cyclohexene-carbaldehyde, containing 35% of 3-(4-methyl-3-pentenyl)-$\Delta^3$-cyclohexene-carbaldehyde, are placed in a three-necked flask provided with a stirrer, thermometer and dropping funnel and 110 g (1.05 mols) of diethanolamine are allowed to flow in over a period of 20 minutes, the temperature rising to 40° C. After the addition, the mixture is further stirred for 1 hour at 40° C.

The mixture is allowed to cool and is taken up in 200 ml of toluene. 20 g of water are decanted off. The toluene phase is concentrated on a rotary evaporator under a pressure of 14 mmHg at 50° C. In this manner there are obtained 280 g of 4-[N-2-hydroxyethyl-oxazolidin-2-yl]-1-(4-methyl-3-pentenyl)-cyclohexene, containing 35% of 5-[N-2-hydroxyethyl-oxazolidin-2-yl]-1-(4-methyl-3-pentenyl)-cyclohexene. The crude material contains 7% of starting material and 1% of unidentified impurities [gas chromatographic determination at 240° C. on a Chromosorb G-column (2% dimethylpolysiloxane)]. According to NMR and IR spectra the purity of the oxazolidine is 97%.

345 g of 50 % sulphuric acid are placed in a 5 liter round-bottomed flask which is provided with a stirrer, thermometer and two dropping funnels. The flask is cooled to −5° C. and 280 g of the crude oxazolidine and 445 g of 61% sulphuric acid are simultaneously added at a temperature between 0° C. and 5° C. The duration of the addition is extended to 1 hour. The mixture is then further stirred for 2 hours at 5° C.

1 liter of cooled toluene is added to the mixture at −10° C. The temperature is kept below 15° C. and 2.2 liters of a 10% sodium hydroxide solution are slowly added until a pH value of 6 is achieved. The mixture is now warmed to 25° C. and stirred at this temperature for 1 hour. The organic phase is decanted, the aqueous solution saturated with sodium chloride and then extracted twice with 1 liter of toluene each time. The toluene phases are washed with a sodium bicarbonate solution and subsequently with water until neutral. The toluene is distilled off at 14 mmHg, there being obtained 204 g of crude product. This product is now crudely distilled a first time (without a column) in the presence of BHT (butylhydroxytoluene) and of calcium carbonate in order to remove the products having low volatility. In this manner there is obtained:

16 g of top fractions of boiling point 100° C./0.7 mmHg 152 g of crude 4-(4-methyl-4-hydroxypentyl)-Δ³-cyclohexene-carbaldehyde of boiling point 105°–130° C./0.7 mmHg 22 g of residue.

The 152 g of crude product are distilled through a 120 mm Widmer column under a vacuum of 0.1 mmHg [in the presence of BHT and calcium carbonate]. In this manner there are obtained 117.4 g of chemically pure aldehyde with the isomer ratio indicated earlier; boiling point 107°–108° C./0.1 mmHg; $n_D^{20}$ = 1.4920–1.4910; yield 56%.

What I claim is:

1. A compound of the formula:

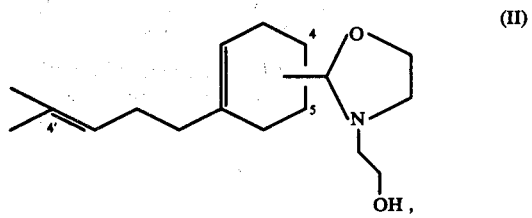

(II)

wherein the N-2-hydroxyethyl-oxazolidinyl group is in the 4- or 5-position, or a mixture of the 4-and 5-position isomers of formula II.

* * * * *